(12) United States Patent  
DeSimone et al.

(10) Patent No.: US 6,885,492 B2
(45) Date of Patent: Apr. 26, 2005

(54) SPATIAL LIGHT MODULATOR APPARATUS (75) Inventors: Andrew Frank DeSimone, Gloucester, MA (US); Bruce Crary, Everett, MA (US)

(73) Assignee: Imaginative Optics, Inc., Gloucester, MA (US)

( * ) Notice: Subject to any disclaimer, the term of this patent is extended or adjusted under 35 U.S.C. 154(b) by 47 days.

(21) Appl. No.: 10/191,947

(22) Filed: Jul. 9, 2002

(65) Prior Publication Data

US 2003/0086145 A1 May 8, 2003

Related U.S. Application Data

(60) Provisional application No. 60/337,801, filed on Nov. 8, 2001.

(51) Int. Cl.$^7$ ............................ G02B 26/00; G02B 21/00
(52) U.S. Cl. ........................................ 359/290; 359/298
(58) Field of Search ................................. 359/290, 292, 359/298, 318, 368, 390, 223; 250/216, 227.26, 201.3; 356/447

(56) References Cited

U.S. PATENT DOCUMENTS

| | | |
|---|---|---|
| 4,561,731 A | 12/1985 | Kley |
| 5,061,049 A | 10/1991 | Hornbeck |
| 5,083,857 A | 1/1992 | Hornbeck |
| 5,535,047 A | 7/1996 | Hornbeck |
| 5,583,688 A | 12/1996 | Hornbeck |
| 5,923,036 A | 7/1999 | Tague, Jr. et al. |
| 5,923,466 A | 7/1999 | Krause et al. |
| 5,933,274 A | 8/1999 | DeSimone |
| 6,038,067 A | 3/2000 | George |
| 6,128,077 A | 10/2000 | Jovin et al. |
| 6,133,986 A | 10/2000 | Johnson |
| 6,144,489 A | 11/2000 | Wilson et al. |
| 6,177,980 B1 | 1/2001 | Johnson |
| 6,211,484 B1 | 4/2001 | Kaplan et al. |
| 6,215,586 B1 | 4/2001 | Clark |
| 6,243,197 B1 | 6/2001 | Schalz |
| 6,249,381 B1 | 6/2001 | Suganuma |
| 6,271,955 B1 | 8/2001 | Atobe et al. |
| 6,381,074 B1 | 4/2002 | Yoshida |
| 6,399,935 B1 * | 6/2002 | Jovin et al. .................. 250/216 |
| 6,552,830 B1 | 4/2003 | Long |
| 2001/0007775 A1 | 7/2001 | Seul et al. |
| 2001/0010843 A1 | 8/2001 | Garner |
| 2001/0030803 A1 | 10/2001 | Engelhardt et al. |
| 2004/0027462 A1 * | 2/2004 | Hing ........................ 348/222.1 |

\* cited by examiner

Primary Examiner—Scott J. Sugarman
Assistant Examiner—Richard Hanig
(74) Attorney, Agent, or Firm—Iandiorio & Teska (57) ABSTRACT

A spatial light modulator apparatus for an optical microscope system including an optical head with a mounting flange for mounting the optical head to a port of the microscope, a DMD for generating a pattern image of light, a light source mount for receiving a source of illumination, and one or more optical elements for directing light from the source of illumination to the DMD and to direct the pattern image generated by the DMD to the microscope. A DMD controller has a digital input and is connected to the DMD for driving the individual micromirrors of the DMD to generate the pattern image. A pattern generation subsystem is configured to output pattern image data and a digital interface is connected between the digital input of the DMD controller and the pattern generation subsystem, the digital interface configured to provide a digital drive signal to the DMD controller corresponding to the pattern image data.

46 Claims, 9 Drawing Sheets

Prior Art

SPATIAL LIGHT MODULATOR APPARATUS

RELATED APPLICATIONS

This application claims priority of U.S. provisional Ser. No. 60/337,801 filed Nov. 8, 2001 entitled AN ILLUMINATION SYSTEM FOR MICROSCOPES WHICH EMPLOYS A SPATIAL LIGHT MODULATOR DEVICE.

FIELD OF THE INVENTION

This invention relates to a spatial light modulator apparatus and system for use in conjunction with an optical microscope.

BACKGROUND OF THE INVENTION

Spatial light modulators such as liquid crystal displays (LCDs) and digital mirror devices (DMDs) (as available from Texas Instruments, for example) are used to modulate incident light into a spatial pattern to form a light image corresponding to an electrical or optical input. DMDs have been successfully incorporated into video projectors and printers, for example. See U.S. Pat. No. 5,535,047 incorporated herein by this reference.

In the field of microscopes, it is often desirable to create a mask pattern to vary the illumination or viewing properties of the microscope using techniques such as transmissive illumination, incident illumination, dark field illumination, bright field illumination, oblique illumination, differentially shaded illumination, phase contrast illumination, differential polarization illumination, and the like. In one example, a technique known as fluorescence recovery after photobleaching (FRAP) involves labeling specific proteins within a living cell with fluorescent dyes and then selected areas are irreversibly photobleached by an intense flash of light and the diffusional mobility of the protein is measured by measuring the fluorescence recovery through the exchange of bleached for non-bleached protein. In this example, a small area of the slide containing the cells is targeted and measured comparatively to the surrounding structure. In this procedure, the ability to control the spatial distribution of the illumination of the microscope for targeting and measurement is critical.

In the past and even today these techniques were accomplished using mechanical pinholes or irises to form the mask pattern image. See U.S. Pat. No. 4,561,731 also incorporated herein by this reference.

After the advent of spatial light modulators such as LCDs and DMDs, however, those skilled in the art soon began proposing these types of modulators in microscope systems instead of pinholes or irises to form mask patterns. A DMD is shown in U.S. Pat. No. 5,535,047 incorporated herein by this reference.

Surprisingly, however, the art is currently limited a) to specially configured microscopes employing LCDs and DMDs, (see, for example, U.S. Pat. Nos. 5,923,036; 5,587,832; and 5,923,466 incorporated herein by this reference) or, alternatively, b) to a microscope coupled to a complete video projector—the video projector itself incorporating, inter alia, an LCD or DMD, a light source, and the associated driver. See U.S. Pat. No. 6,243,197 incorporated herein by this reference.

The drawbacks to such configurations are many. Specially designed microscopes are expensive and render obsolete the user's existing microscopes. Video projector type illuminating devices coupled to an existing microscope, on the other hand, results in an unduly complex, bulky, and expensive design, and, moreover, results in flickers and restrictions on the range of wavelengths which can be used in the microscope due to, inter alia, both the video projector design and the video input signal which operates the video projector.

For example, the use of a commercially available video projector with a DMD controlled by a computer graphics card for illumination in a microscope (U.S. Pat. No. 6,243,197) has significant drawbacks. Since video projectors typically use a rotating color wheel between the light source and the DMD, the micromirrors must be synchronized to the primary color segments of the spinning wheel. This type of illumination inherently 'flickers' and, although acceptable for overhead projections, is not adequate for scientific microscopy. The temporal switching inherent in the method of pulse-width modulation (PWM) used to vary intensity levels in a projector system, combined with the electrical noise of the computer graphic card interface, may result in unacceptable flicker in a microscope system. Furthermore, the spectral nature of the light source and optical coatings used in video projectors would restrict microscope studies to a wavelength range narrower than usual.

What is needed is an optical head which can be easily coupled to a wide variety of existing microscopes and employing DMD or other spatial light modulation technology to digitally generate mask patterns in real time and without the necessity of the other components and the limitations associated with video projectors. Such a spatial light modulator apparatus is useful, for example, when carrying out FRAP and other techniques and procedures.

SUMMARY OF THE INVENTION

It is therefore an object of this invention to provide a spatial light modulator apparatus which is less complex than a complete video projector unit with the necessary modification and additions, which is lower in cost, and which performs better.

It is a further object of this invention to provide such an apparatus which is useful with and easily coupled to existing microscopes.

It is a further object of this invention to provide such an apparatus and indeed even a complete system which typically requires little or no modification of the user's existing microscope.

It is a further object of this invention to provide such an apparatus and system which can be easily tailored to the user's specific microscope.

It is a further object of this invention to provide such an apparatus which employs the high pixel density and wide spectral bandwidth of current and future DMD technologies without the need for a separate projector.

It is a further object of this invention to provide such an apparatus which interfaces directly with the DMD.

It is a further object of this invention to provide such an apparatus which eliminates the flicker associated with video projectors.

The invention results from the realization that instead of designing specially configured microscopes or coupling a complete video projector to an existing microscope, a lower cost spatial light modulator which produces mask pattern images in real time is effected by the combination of a specially designed optical head itself incorporating a DMD and a DMD controller digitally controlled by a digital interface responsive to a computerized pattern generation subsystem to provide a digital drive signal to the DMD controller corresponding to pattern image data produced by the pattern generation subsystem.

Instead of a video projector responsive to an analog VGA signal output from a computer graphics card as set forth in the '197 patent, the present invention operates solely in the digital realm by the use of a DMD interface which, in essence, provides to the DMD controller a map of DMD mirror settings corresponding to the mask pattern desired by the user. In this way, the illumination lamp need not be integral with the modulator apparatus and instead a wide variety of light source inputs may be used. Moreover, the complexity and cost of the modulator apparatus is severely reduced, the DMD controller is now a simple buffer, the modulator apparatus can be mounted to either the reflected light port, the transmitted light port, or the camera port of the microscope, a laser light input can even be used, and real time imaging accomplished.

This invention features a spatial light modulator apparatus for an optical microscope system, the apparatus comprising an optical head including a mounting flange for mounting the optical head to a port of the microscope, a spatial light modulator device such as a DMD for generating a pattern image of light, a light source mount for receiving a source of illumination, and one or more optical elements for directing light from the source of illumination to the DMD and to direct the pattern image generated by the DMD to the microscope. A DMD controller has a digital input and is connected to the DMD for driving the individual micromirrors of the DMD to generate the pattern image. A pattern generation subsystem is configured to output pattern image data and a digital interface is connected between the digital input of the DMD controller and the pattern generation subsystem and configured to provide a digital drive signal to the DMD controller corresponding to the pattern image data.

Preferably, the DMD controller is mounted on the optical head adjacent the DMD and the digital interface is housed on a PC card received in a computer and the pattern generation subsystem is operable on the computer.

In one example, the optical head includes a housing with an illumination axis, the DMD is located on the housing on the illumination axis thereof and the mounting flange is located on the housing on the illumination axis thereof opposite the DMD. The light source mount is typically located on the optical head housing on an axis transverse to the illumination axis. In the same example, the optical head further includes a light baffle positioned such that when the micromirrors of the DMD are in the off state, light reflected by the DMD is directed to the light baffle. The optical microscope has a field plane and the DMD and the optical elements of the optical head may be configured to direct the pattern image generated by the DMD to the field plane of the optical microscope. Alternatively, the DMD and the optical elements of the optical head are configured to direct the pattern image generated by the DMD to a conjugate of the field plane of the optical microscope.

A camera is typically attached to the microscope, the camera having a field of view and the optical elements of the optical head are configured such that the DMD pattern image fills part or all of the field of view of the camera.

A light source is typically disposed in the light source mount such as a halogen lamp, a flash lamp, an arc lamp, or a laser light source. In the preferred embodiment, the light source mount further includes a shutter assembly and a filter holder assembly. The optical head may further include a secondary light source mount also with a shutter assembly and a filter holder assembly. The optical head may further include a beam splitter mount.

In the preferred embodiment, the digital interface includes a clock which provides a clock signal and a logic device responsive to the pattern image data and the clock signal and configured to assign pixels to the pattern image data and to serialize the assigned pixels according to the clock signal to reformat the pattern image data to correspond to the spatial addressing of the DMD and is further configured to generate a plurality of timing signals based on the clock signal to synchronize serialization of the assigned pixels. The plurality of timing signals typically correspond to DMD address counter signals. Several of the plurality of timing signal may be multiplied in frequency by the logic device to provide faster global dark resets of the mirrors of the DMD. In the preferred embodiment, the logic device is a field programmable gate array and a digital cable connects the digital interface to the digital input of the DMD controller. The DMD controller is configured to buffer the reformatted mask image data and to load the memory cells of the DMD. The DMD controller is further configured to provide a reset command, a new state command, and a hold command to reset, new state, or hold, respectively, all of the mirrors of the DMD simultaneously.

In one example, the optical microscope includes a camera for imaging the specimen viewed by the microscope live on a display. The pattern generation subsystem is configured to output pattern image data and comprises a drawing editor responsive to an input device for drawing a pattern shape and an alpha blending routine responsive to the camera and the drawing editor for representing the drawn pattern shape translucently on the display over the specimen image. The digital interface is responsive to the drawing editor to provide a digital drive signal which controls the DMD to generate the pattern image which is identical in shape to the translucent pattern shown on the display. The pattern generation subsystem typically further includes a set of stored calibration values and a spatial scale and offset routine interposed between the drawing editor and the digital interface and responsive to the stored calibration values for correlating the pixels of the drawn pattern shape to the pixels of the DMD. This invention also features an optical head for a spatial light modulator system, the optical head comprising a mounting flange for mounting the optical head to a port of the microscope, a spatial light modulator device for generating a pattern image of light, a light source mount for receiving a source of illumination, one or more optical elements for directing light from the source of illumination to the spatial light modulator device and to direct the pattern image generated by the spatial light modulator device to a microscope, and a controller connected to the spatial light modulator device for driving the spatial light modulator device to generate the pattern image, the controller having a digital input responsive to a digital drive signal. Typically, the spatial light modulator device is a DMD located on the housing on the illumination axis thereof and the mounting flange is located on the housing on the illumination axis opposite the DMD.

This invention also features a digital interface interconnected between a controller for a spatial light modulator device (e.g. a DMD) and a pattern generation subsystem, the digital interface comprising a clock which provides a clock signal and a logic device responsive to pattern image data output by the pattern generation subsystem and the clock signal and configured to assign pixels to the pattern image data and to serialize the assigned pixels according to the clock signal to reformat the pattern image data to correspond to the spatial addressing of the spatial light modulator device and the logic device is further configured to generate a plurality of timing signals based on the clock signal to synchronize serialization of the assigned pixels. The plurality of timing signals usually correspond to DMD address counter signals and several of the said DMD address counter signals are preferably multiplied in frequency by the logic device to provide faster global dark resets. Typically, the logic device is a programmable logic device or a field programmable gate array and further included is a digital cable connecting the digital interface to a DMD controller connected to the DMD. The DMD controller is preferably configured to buffer the reformatted pattern image data and to load the memory cells of the DMD. The logic device may be further configured to provide a reset command, a new state command, and a hold command. Preferably, the digital interface is on a PC card received in a computer and wherein the pattern generation subsystem is operable on the computer.

This invention also features a pattern generation subsystem configured to output a pattern image data to a spatial light modulator (e.g., a DMD), the pattern generation subsystem comprising a drawing editor responsive to an input device for drawing a pattern shape and an alpha blending routine responsive to a camera and the drawing editor for representing the drawn pattern shape translucently on a display over a specimen image. A digital interface may be included responsive to the drawing editor to provide a digital drive signal which controls the spatial light modulator to generate the pattern image. Further included is a set of stored calibration values and a spatial scale and offset routine interposed between the drawing editor and the digital interface and responsive to the stored calibration values for correlating the pixels of the drawn pattern shape to the pixels of the spatial light modulator.

In a preferred embodiment, a spatial light modulator system for an optical microscope, in accordance with this invention, features an optical head including a mounting flange for mounting the optical head to either the reflected light port or the transmitted light port of the microscope, a spatial light modulator for generating a pattern image of light, a light source mount for receiving a source of illumination, and one or more optical elements for directing light from the source of illumination to the spatial light modulator and to direct the pattern image generated by the spatial light modulator to the microscope. A controller is mounted on the optical head adjacent the spatial light modulator and has a digital input. A computer includes a pattern generation subsystem configured to output pattern image data and a digital interface PC card configured to provide a digital drive signal to the controller corresponding to the pattern image data generated by the pattern generation subsystem.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

Figure 1:
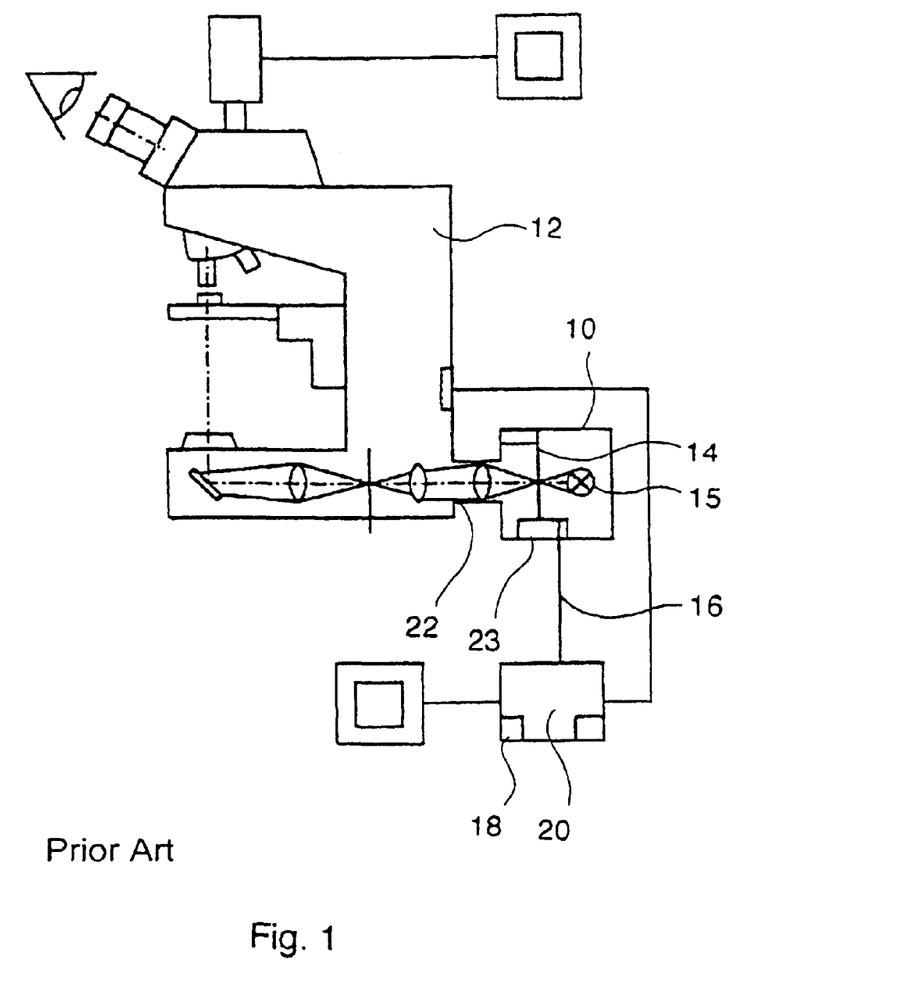
FIG. 1 is schematic view of a prior art lighting device for a microscope employing a complete video projector as set forth in U.S. Pat. No. 6,243,197.

Prior art lighting device 10, FIG. 1 for microscope 12 is a complete video projector unit purporting to employ LCD or DMD 14, light source 15, and drive 23 connected via video cable 16 to graphic card 18 of "control/calculating device" 20. Device 10 is connected to transmitted light port 22 of microscope 12 and graphics card 18 generates the image signal for driving LCD/DMD 14. The other components of this system are described in U.S. Pat. No. 6,243, 197. The drawbacks, limitations, and problems associated with such a system are discussed in the background section above.

Figure 2:
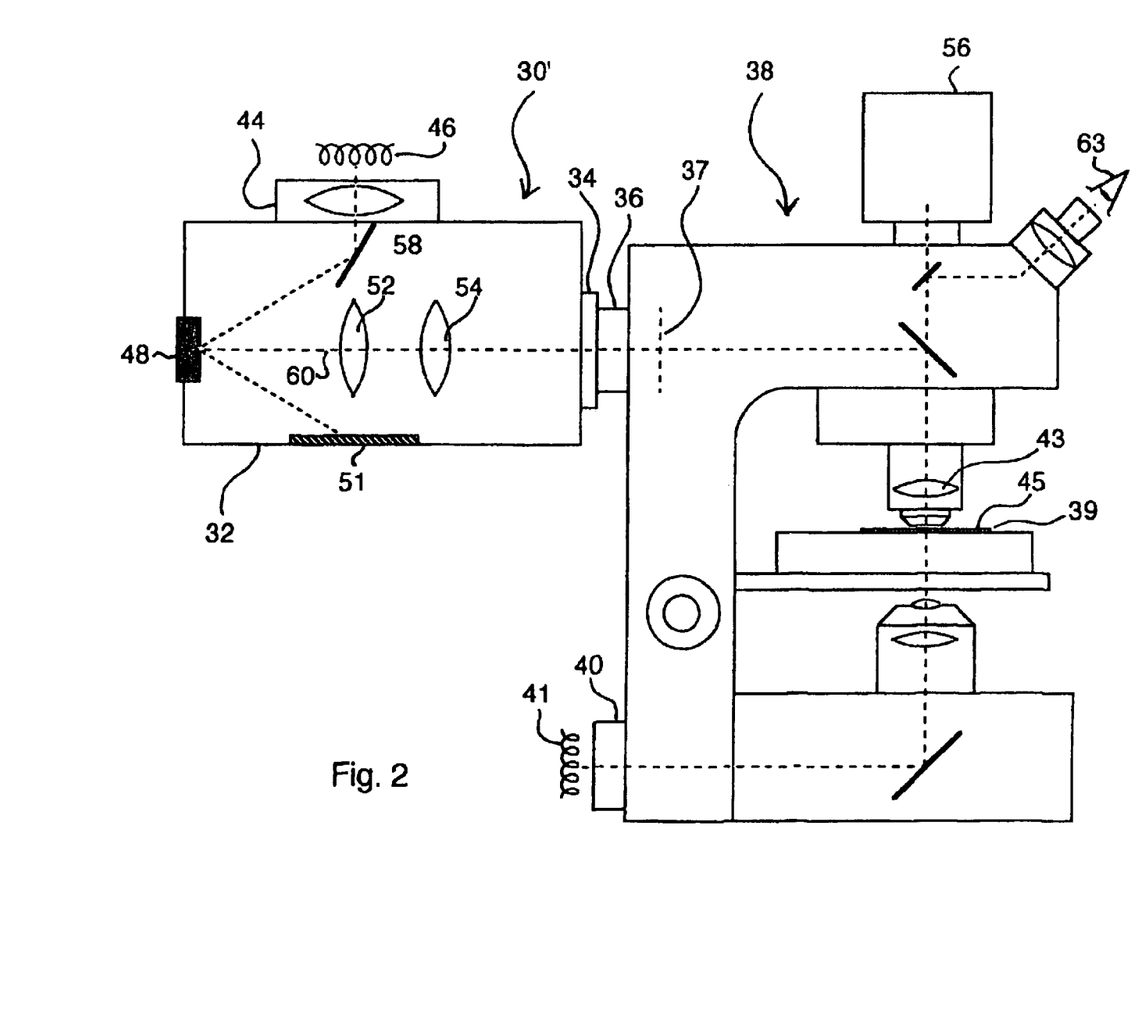
FIG. 2 is a schematic view showing the primary components associated with one embodiment of the spatial light modulator apparatus of the subject invention and, in particular, the optical head thereof.

In this invention, the spatial light modulator apparatus, in one embodiment, includes optical head 30, FIG. 2 with housing 32 having mounting flange 34 thereon for mounting optical head 30 to the reflected light port 36 of microscope 38. Optical head 30 may alternatively be mounted to port 40 instead of transmitted light source 41, or even camera port 42 typically employing camera 56.

Light source mount 44 receives a source of illumination 46 such as a halogen lamp, a flash lamp, an arc lamp, or even a laser light source. Light from illuminated light source 46 is directed to a spatial light modulator device, preferably DMD 48 via optical element 58 (e.g., a mirror) and the pattern generated by DMD 48 is directed via optical elements 52, 54 (e.g., refractive or reflective optical elements or a combination of both) to microscope 38. Light baffle 51 is positioned as shown such that when the micromirrors of DMD 48 are in the off state, light reflected by DMD 48 is directed to light baffle 51.

Thus, optical head 30 contains the optical subsystem which serves to optically relay the image generated by DMD 48 to field plane 37 or to a conjugate of field plane 37 of microscope 38. Since field plane 37 is conjugate to specimen plane 39, the image of the surface of DMD 48 is projected onto specimen plane 39. Each spatial position on the surface of DMD 48 is represented by a spatial position on specimen 45 located at specimen plane 39. The size of that representation is dependent upon the magnification factors of the optical subsystem including optical elements 52 and 54 and the magnification factors of the reflected light port 36 and objective 43 of microscope 38. The magnification factors in the reflected light and transmitted light portions of microscope 38 differ between different microscope models. Thus, the optical subsystem including optical elements 52 and 54 may be adjustable such that the image size of DMD 48 remains within usable limits. If the DMD image greatly overfills the entire field of view, the spaces between the micromirrors may become apparent to the user and illumination of specimen 45 may have a lattice-like appearance. If the DMD image significantly underfills the field of view, the benefits of the subject invention may likewise not be realized. Thus, ideally, the DMD image should fill the entire field of view of camera 56.

In the particular embodiment shown, housing 32 defines illumination axis 60 and DMD 48 is located on housing 32 on illumination axis 60 and mounting flange 34 is located on housing 32 opposite DMD 48 but also on illumination axis 60. Light source mount 44 is located on housing 32 on an axis which intersects illumination axis 60 at DMD 48.

Figure 3:
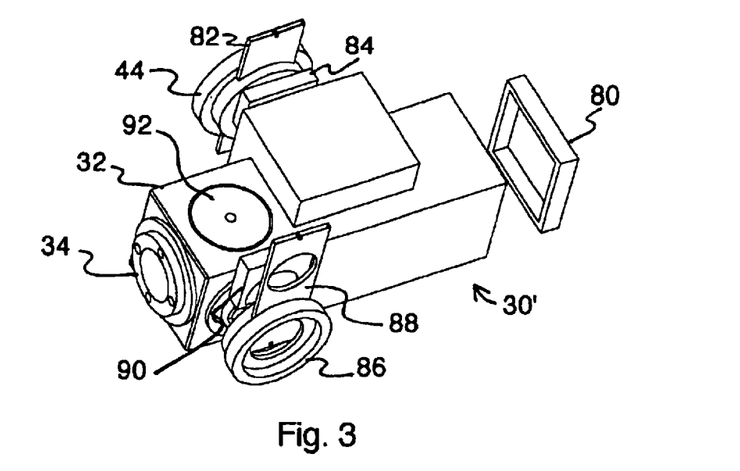
FIG. 3 is a schematic top side view of another embodiment of the optical head of the subject invention.
Figure 4:
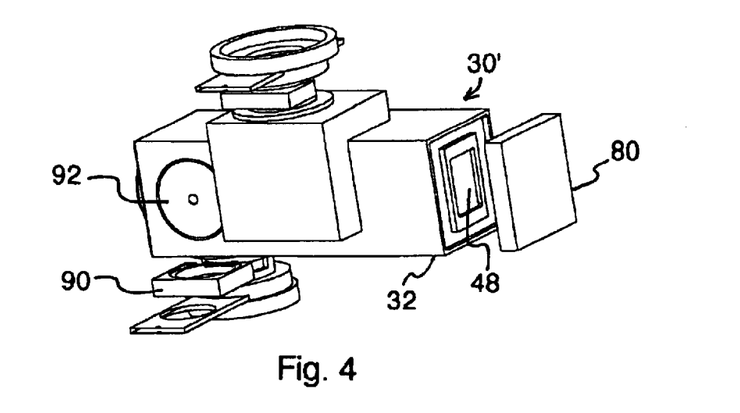
FIG. 4 is a schematic rear view of the optical head shown in FIG. 3.
Figure 5:
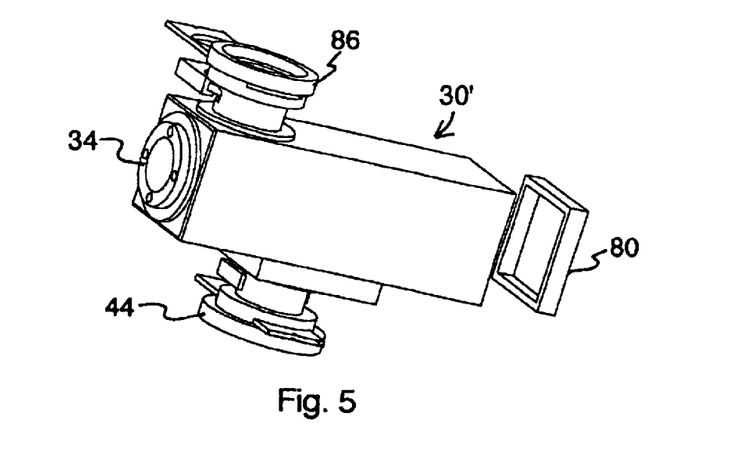
FIG. 5 is a schematic bottom side view of the optical head shown in FIGS. 3 and 4.

In the prototype design shown in FIGS. 3–5, DMD controller 80, FIG. 4 is mounted on optical head 30 adjacent to DMD 48 and further included is shutter assembly 82 and filter holder assembly 84, FIG. 3 for light source mount 44. Shown in FIG. 3 is secondary light source mount 86 with shutter assembly 88 and filter holder assembly 90, and beam splitter mount 92. See U.S. Pat. No. 5,933,274 incorporated herein by this reference.

Figure 6:
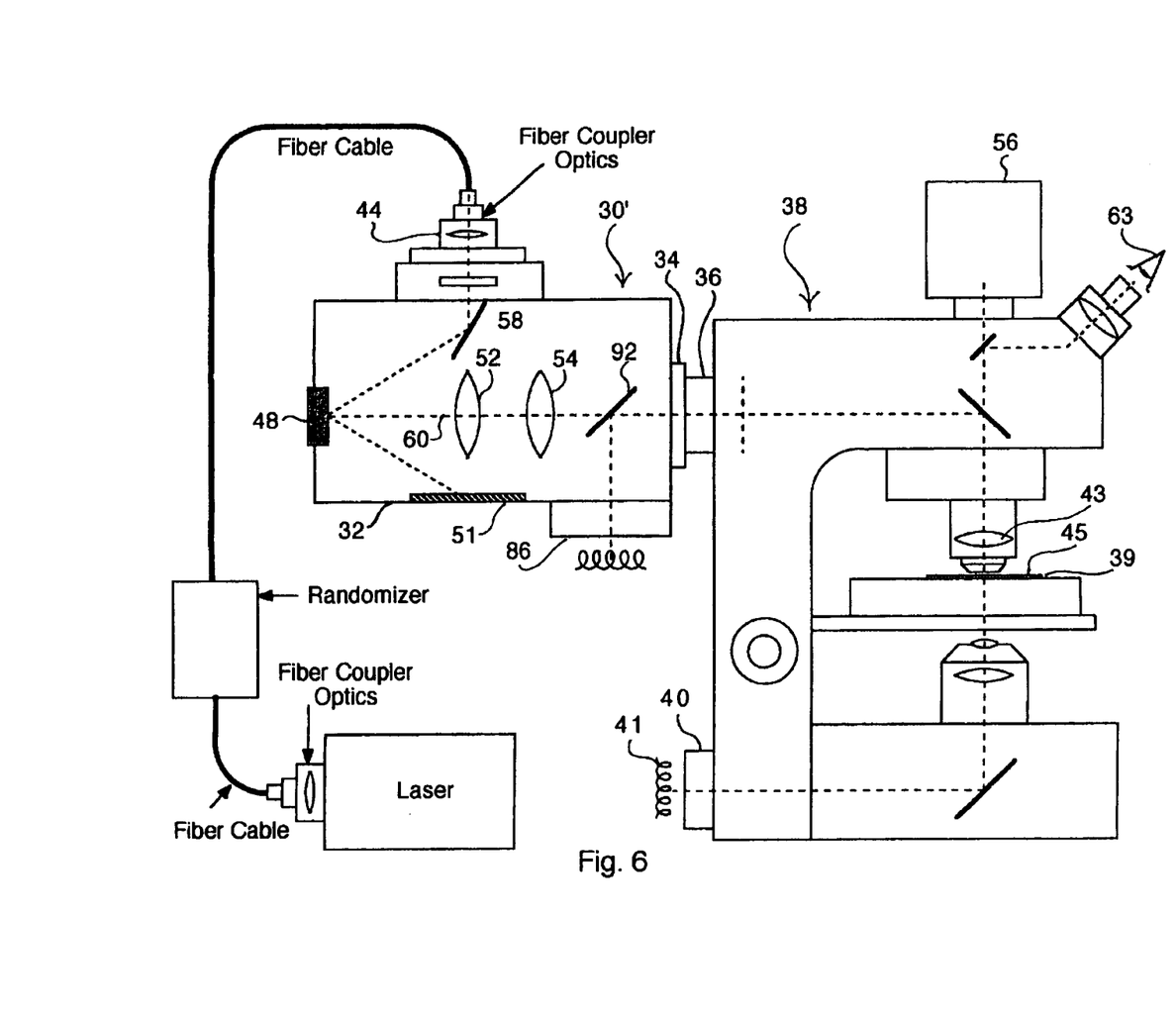
FIG. 6 is a schematic view showing the optical head of FIGS. 3–5 coupled to a microscope and a laser light source coupled to the optical head in accordance with the subject invention.

FIG. 6 is a block diagram of the embodiment shown in FIGS. 3–5 mounted on microscope 38 and further showing a laser illumination source attached to light source mount 44. Beam splitter mount 92 allows the placement of an optical element which permits the mask pattern image generated by DMD 48 to pass through and into microscope 38 while also receiving illumination from a secondary light source attached to secondary light source mount 86 and directing that illumination into microscope 38 in a manner coaxial with the mask pattern generated by DMD 48. Thus, specimen 45 on microscope 38 can be illuminated overall in a conventional manner with one light source and simultaneously illuminated with a mask pattern.

Figure 7:
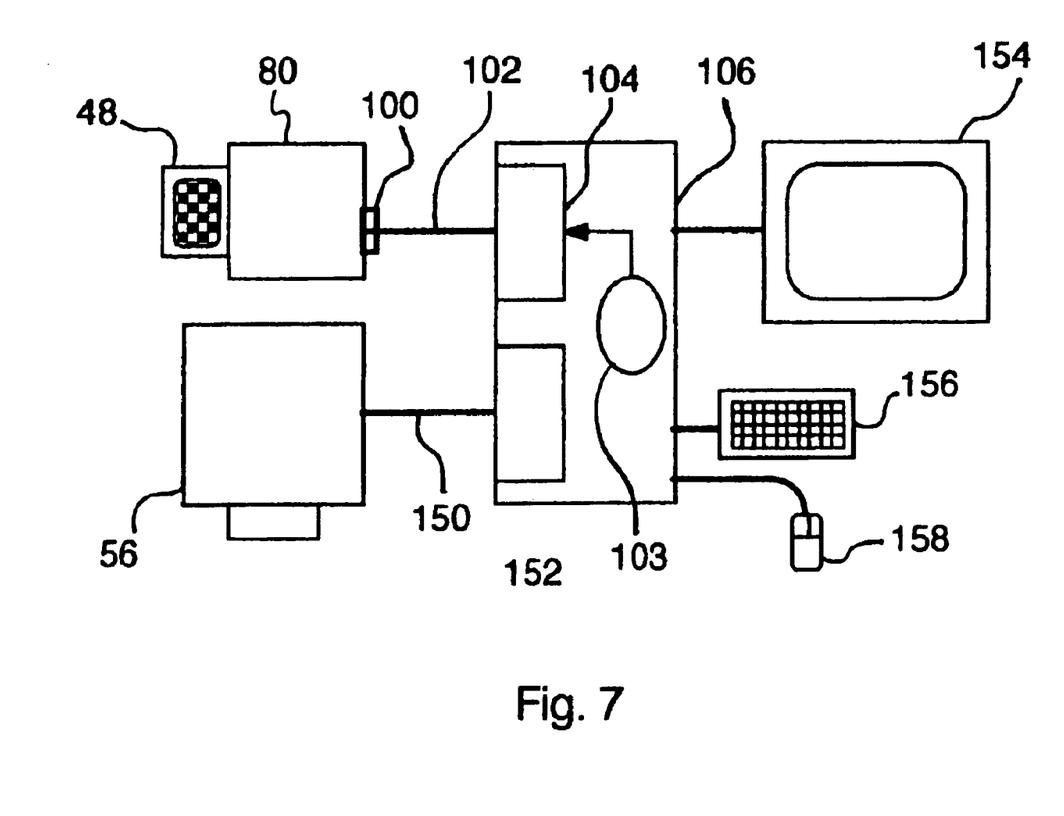
FIG. 7 is a block diagram showing the primary components associated with a complete spatial light modulator apparatus in accordance with the subject invention.

A complete spatial light modulator apparatus in accordance with this invention also features DMD controller 80, FIG. 7 having digital input connector 100 connected to digital interface 104 of computer 106 via digital interface cable 102. Pattern generation subsystem 103 also operating on computer 106 and discussed in further detail below is configured to output pattern image data to digital interface 104 which provides a digital drive signal to DMD controller 80 via digital cable 102 corresponding to the pattern image data. DMD controller 80, in turn is connected to DMD 48 and drives the individual micromirrors of DMD 48 to generate the pattern image transmitted via optics 52 and 54, FIGS. 2 and 6, to microscope 38.

Figure 8:
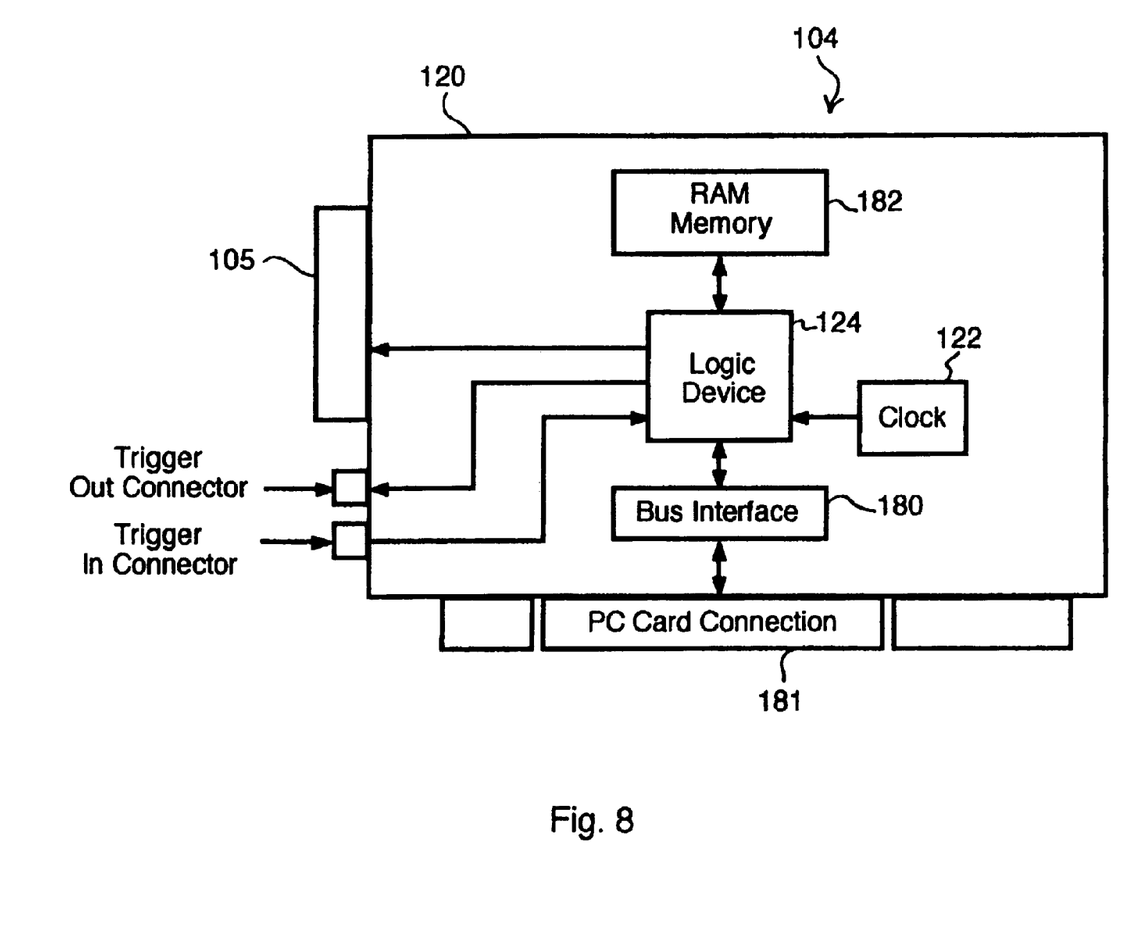
FIG. 8 is a block diagram showing the primary components associated with the digital interface of the apparatus shown in FIG. 7.

In one embodiment, digital interface 104, FIG. 7 is housed on PC card 120, FIG. 8 received in computer 106, FIG. 7 and has digital output connector 105 connected to digital cable 102, FIG. 7. As shown in FIG. 8, digital interface 104 includes clock 122 which provides a clock signal to logic device 124 (e.g., a field programmable gate array (FPGA)). Logic device 124 is responsive to pattern image data provided by the pattern generation subsystem 103 via computer bus interface 180 and PC Card connection 181 and the clock signal and is configured to assign pixels to the pattern image data and to serialize the assigned pixels according to the clock signal to reformat the pattern image data to correspond to the spatial addressing of DMD 48. DMD controller 80, FIG. 7 is configured to buffer the reformatted mask image data and to load the static-RAM (SRAM) memory cells of DMD 48. Logic device 124, FIG. 8 of digital interface 104 is also configured to generate a plurality of timing signals based on the clock signal to synchronize serialization of the assigned pixels. In the preferred embodiment, the plurality of timing signals correspond to DMD address counter signals but may be multiplied in frequency by logic device 124 to provide faster global dark resets of the mirrors of DMD 48, FIG. 7. Logic device 124, FIG. 8 is preferably configured to provide a reset mirror command, switch to a new mirror state command, and a hold mirror state command to reset, new state, or hold all of the mirrors of DMD 48, FIG. 7 simultaneously.

Referring again now to FIG. 7, pattern generation subsystem 103, namely software operating on computer 106, is configured to output pattern image data to digital interface 104 which provides the digital drive signal on digital cable 102 to DMD controller 80 corresponding to the pattern image data. Pattern generation subsystem 103 provides a bitmapped mask image 170, FIG. 9 containing an informational mode header. Camera 56, FIG. 7 which is mounted on the microscope is connected via camera cable 150 to camera interface 152 located within computer 106. Camera interface 152 may be a frame grabber type card to interface to analog camera video signals, to digitize those signals into video data, and to distribute that data into the computer data bus. In another embodiment, camera interface 152 is a digital device such as an IEEE 1394 interface to allow use of cameras compliant with the IEEE 1394 digital communications standard.

Typically, each DMD 48 contains an array of several hundred thousand micromirrors on the surface. Each micromirror is typically 16 microns square and separated from each other by a 1 micron space. Each micromirror is addressable electronically. With a logic state of high in the SRAM beneath the micromirror, the micromirror tilts to a positive 10° position, typically, which herein is called the "on" state. With a logic state of low, the micromirror tilts to a negative 10° position, typically, which herein is called the "off" state. The light emitted from light source 46, FIG. 2 which is incident on the off state micromirrors of DMD 48 is reflected along an axis other than illumination axis 60 into light baffle 51. In the case of the "on" state micromirrors, light emitted from light source 46 is reflected from these micromirrors of DMD 48 along illumination axis 60 into microscope 38. The light is then directed to specimen plane 39 by microscope 38, illuminating specimen 45 in a pattern matching the "on" micromirrors of DMD 48. The size of the illuminated pattern is dependent on the optical magnification factors mentioned above.

For the purposes of illustration, assume that specimen 45 is somewhat reflective, light source 46 is turned on and the micromirrors of DMD 48 representing the pattern "X" are in the "on" state. The image at eye point 63 is the image of specimen 45 superimposed on the image of the micromirror pattern "X" of DMD 48. The same image is present at camera 56 and at computer monitor 154, FIG. 7. If objective 43, FIG. 2 of microscope 38 is changed to one of a higher magnification, the image of specimen 45 at the same locations will be larger but the pattern "X" image of the array of micromirrors of DMD 48 will not change in size at eye point 63.

In the art, the term "pixel" is used in a variety of contexts. For example, the manufacturer of DMD 48 calls each micromirror a pixel, DMD 48 is said to break the light into a plurality of separate regions called pixels, the digital video image of specimen 45 under microscope 38 is composed of pixels, and monitor 154, FIG. 7 is resolved into pixels. To avoid confusion, the following nomenclature is used herein. The spatial representation of each micromirror of DMD 48, FIGS. 2 and 7 is called a DMD pixel, and the spatial representation of the image acquired by video camera 56 and viewed on computer monitor 154 is called a screen pixel.

Using keyboard 156 and computer mouse 158 in conjunction with the custom software 103 of this invention, the user is able to control specimen illumination. Software 103 controls DMD 48 by way of digital interface 104, digital interface cable 102 and DMD controller 80.

Figure 11:
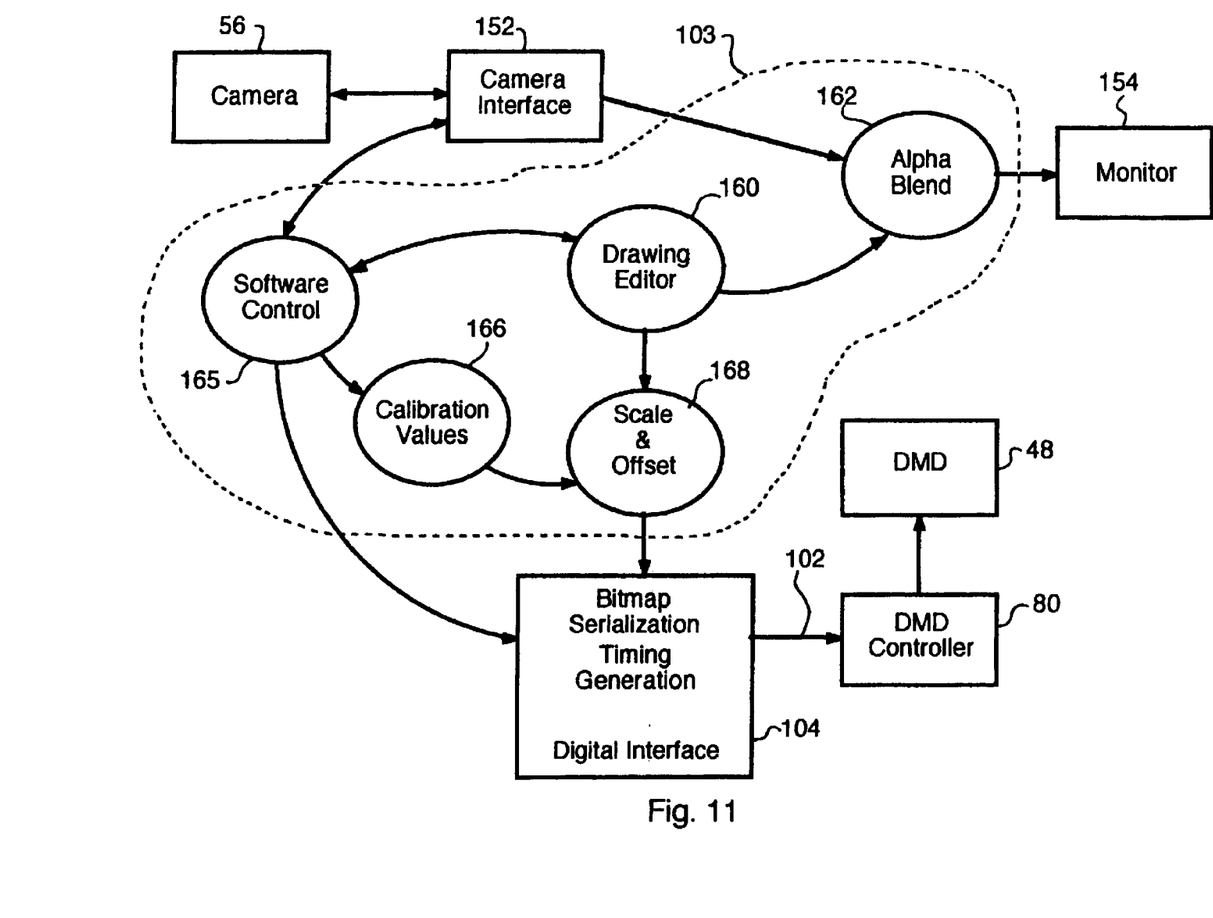
FIG. 11 is a diagram showing the interrelation between the various computer software and hardware components of a complete system in accordance with the subject invention.

Software 103, FIG. 11 displays on monitor 154 a live video image of the specimen captured by camera 56 transmitted over camera cable 150 to camera interface 152. The live video image of the specimen is displayed on monitor 154 for reference only in order to target what areas are to be masked. By using mouse 158 and the drawing editor 160 portion of software 103, the user has the ability to draw translucent mask-overlays of any desired shape which superimpose upon the image of the specimen. The user will still be able to see the live video image underneath the translucent mask overlay. The user will also be able to select from a set of pre-defined translucent mask-overlays (including full-field) or to select and recall user-defined translucent mask-overlays from stored computer files. The user can than select to have the specimen illuminated in a pattern identical to the shape of these overlays.

Drawing editor 160 of pattern generation subsystem 103, FIG. 11 is responsive to keyboard 156, FIG. 7 or mouse 158 or any other input device for drawing a pattern shape. Alpha blending routine 162, FIG. 11, is responsive to camera 56, FIG. 7 (via camera interface 152) and drawing editor 160, FIG. 11 for representing the pattern drawn using drawing editor 160 translucently on the display or monitor 154 over the specimen image acquired by camera 56. Thus, digital interface 104, FIG. 7 is responsive to drawing editor 160, FIG. 11 to provide a digital drive signal which controls DMD 48, FIG. 7 via DMD controller 80 to generate a pattern mask image which represents the translucent pattern shape. Pattern generation subsystem 103 may further include a set of stored calibration values 166, FIG. 11 and a spatial scale and offset routine 168 interposed between drawing editor 160 and digital interface 104 to be responsive to the stored calibration values 166 for correlating the screen pixels of the drawn pattern shape to the pixels of DMD 48.

More specifically, drawing editor 160, FIG. 11 preferably generates data for the mask-overlay image to be displayed on monitor 154 and also combines that data with calibrated spatial scale and offset information via routine 168 and the calibration values stored at 166 to form a solid mask image to be transferred to DMD 48. The three images are separate sets of data, the specimen image is solid, the mask-overlay image is translucent and is overlayed upon the specimen image and thirdly, the mask image is solid, scaled, and offset.

Scale and offset routine 168 in connection with calibration values 166, allows scaling and offset in two spatial axes, in order to achieve accurate and repeatable registration between screen pixels in the translucent mask-overlay and the DMD pixels. DMD pixels correspond optically to the spatial positions at specimen plane 39, FIG. 6 which correspond to camera pixels which correspond back to screen pixels on the live video image on monitor 154, FIG. 11. In this way, targeting of the desired areas may be done in advance of the illumination sequence with accuracy. Calibration is not required on a frequent basis, but typically preformed only at the time of set-up of the system or upon changing optical subsystem 52, 54, FIG. 2. Drawing editor 160, FIG. 11 data for the mask-overlay image are sent through alpha blending routine 162 to produce desired translucently and then displayed on monitor 154. Drawing editor 160 data is also sent through scale and offset routine 168 and then directed to digital interface 104 over the data bus of the computer.

As stated above, digital interface 104 incorporates logic device 124, FIG. 8 such as a field programmable gate array (FPGA). Digital interface 104 reformats the mask image data to correspond with the spatial addressing of DMD 48, FIG. 11, creates timing and control sequences and provides the reformatted data and sequences to DMD controller 80 via digital interface cable 102. DMD controller 80, FIG. 10 buffers the mask image data and sequences, loads the memory cells of DMD 48, and provides additional control signals and voltages required by DMD 48.

Software 103, FIG. 7 allows the user to control the timing of the illumination in a format such as with pull-down menus. Predetermined and user-defined timing schedules are available to the user. Automatic, manual, and externally triggered modes of operation are possible.

Thus, drawing editor 160, FIG. 11 is used to draw a mask image, and scale and offset routine 168 processes that image according to the stored calibration values 166. This output to digital interface 104 is in the form of a bitmap image and added to the image may be an instructional mode header from software control module 165, FIG. 11 to designate the operational mode (single mask image, multiple repetitions of the image, "live" mode where the mask is generated as fast as possible while the user manipulates drawing editor 160) and information about how the mask image is to be produced such as start time, duration of mask (on time) internal or external trigger, and/or trigger out selection (for triggering the user's light source or detector). This block of data may be transferred over the computer PCI bus by a standard technique called direct memory access (DMA) 190, FIG. 9 to digital interface 104.

Alternatively, the mask image could be in the form of vectorized data instead of bitmap data. For instance the coordinates for the corners of a shape such as a square would transfer faster over DMA. Then, however, logic device 124 of digital interface 104 would have the additional task of bitmapping the data to correspond with the DMD array and "OR"-ing that data to the RAM memory to over-write only the areas changed from the last frame. The serialization of data by the FPGA for output to the DMD controller would remain the same.

Figure 9:
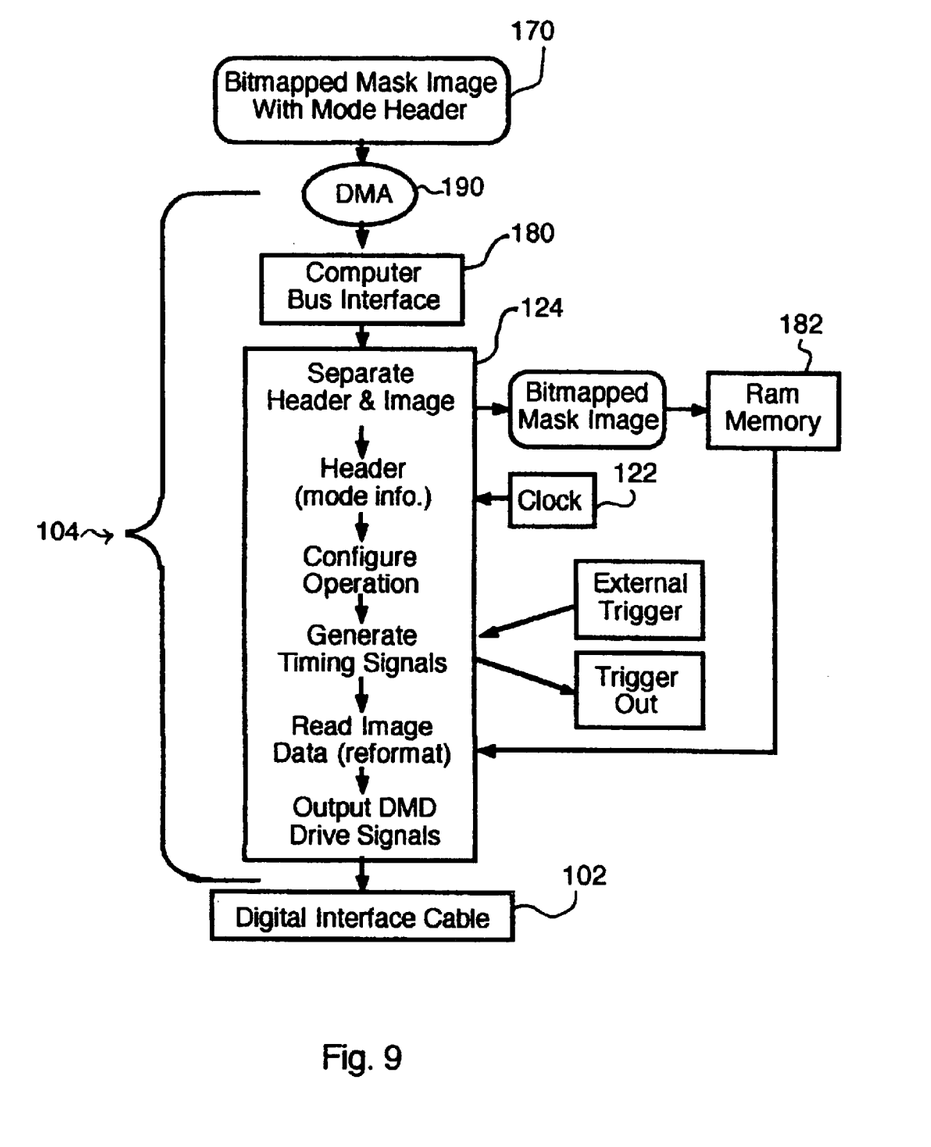
FIG. 9 is a functional flow chart depicting the operation of the digital interface shown in FIG. 8.

Digital interface 104, FIGS. 8 and 9 thus preferably has PC interface 180 which listens to the computer bus. The block of data flows through PC interface 180 and through logic device 124. Logic device 124 functions to strip off and retain the informational mode header, allowing the bitmap data to flow into random access memory (RAM) 182 as shown in FIG. 9. Logic device 124 then uses clock 122 to generate the appropriate counter reset signals (timing generation) and synchronously reads bitmap data out of RAM 182 in a serial fashion; for example, 9600 bits long×50 channels wide, consistent with the structure of the DMD addressing scheme. These data along with the timing signals are sent out over digital interface cable 102, FIG. 7 through DMD controller 80 and into the SRAM addresses on DMD 48. When this is done, according to the operation mode set (trigger, duration, and the like) logic device 124, FIG. 8 issues a "Mirror drive command" which, when interpreted by DMD controller 80, FIG. 10 causes the micromirrors of the DMD 48 to reset, then read their new states from the DMD SRAM addresses, tilt to those new states, and hold until the next such command.

At some time specified by the operator, through external trigger or software (duration), according to the mode, the DMD will be requested to go dark. The quicker the DMD can go dark again after displaying a mask, the better the performance in a situation requiring a brief pulse of light. In the conventional manner of controlling a DMD device, the "Dark" is a global command line wired to the DMD through the DMD controller. The Dark command essentially writes logic state low to all of the RAM addresses on the DMD during a sequence of timing signals regardless of data input states. Since the addresses are selected by the timing signals, the effect is not instantaneous but normally distributed over 640 clock cycles. In the system of the present invention, logic device 124 will issue a Dark sequence, logic device 124 will hold the Dark command high, and further generate specially compacted timing signals (compacted by a factor of four) to allow global addressing of the Dark command four times faster than normal. The logic device need not disturb the bitmap image in RAM memory 182 from the last mask image. For repetitive mode, logic device 124 functions as described above. For live mode, logic device 124 will not enter the Dark sequence, but communicates with the software over bus interface 180 to indicate that an image has been sent to DMD controller 80, FIG. 7 and a Mirror drive command issued. This command instructs the software to begin another sequence of data block (bitmap image and header) transferred via DMA to digital interface 120, FIG. 8. In this way, when the operator is drawing or moving a drawn shape with drawing editor 160, FIG. 11, the mask will track those movements as fast as the system will allow with no dark frames in between.

Figure 10:
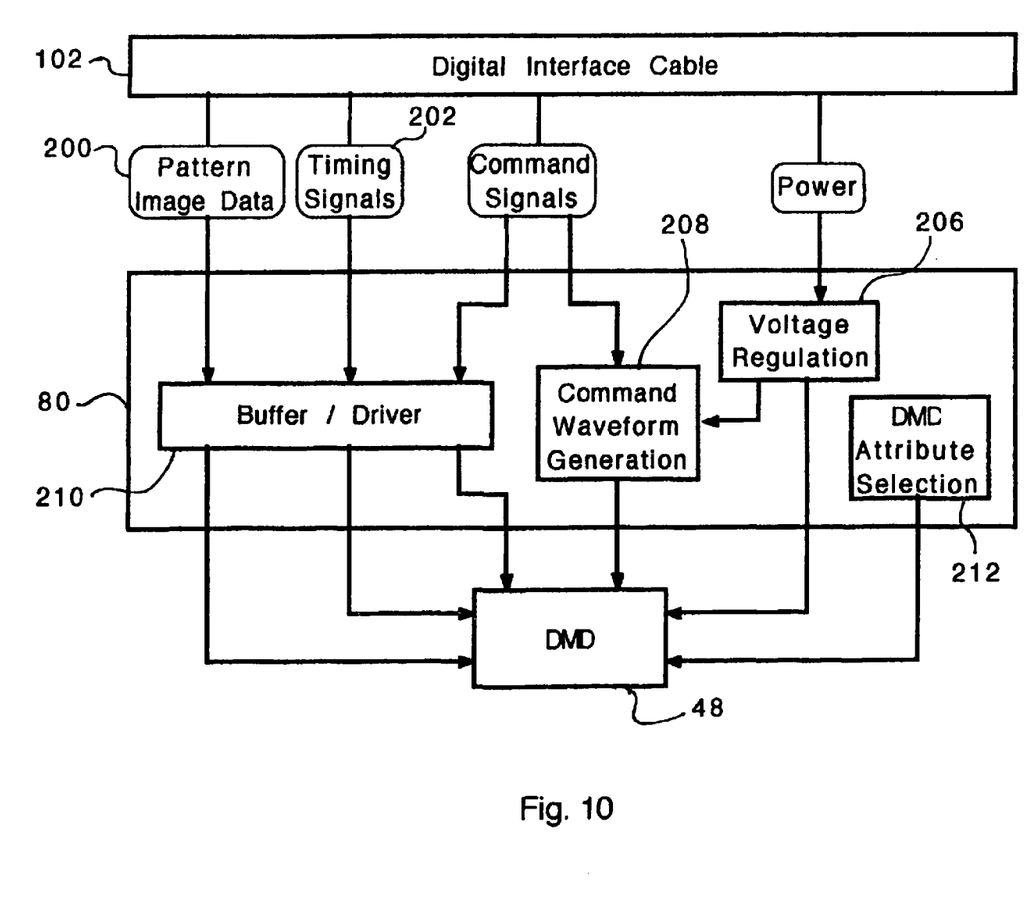
FIG. 10 is a block diagram showing the primary components associated with the DMD controller of this invention.

DMD controller 80, FIG. 10 is connected to digital interface cable 102 as discussed above and appropriately buffers the pattern image data 200 as shown at 210 along with the timing signals 202 and Dark signal and sends them to DMD 48. It also converts the Mirror drive command signals to the high voltage analog waveform as shown at 208 required to electrostatically tilt the mirrors of DMD 48. Although DMD 48 is further divided into fifteen groups of rows, each with its Mirror drive command line, all of these lines are actuated simultaneously for even illumination. Note that Texas Instruments, the manufacturer of the preferred DMD 48, activates these groups in sequence to take advantage of the writing of each column from top to bottom. The row group is written to, and then, while the next row group is being written to, the Mirror drive command for the first group is issued. This, however, results in the image being drawn in blocks from top to bottom whereas in the system of this invention the image appears all at once.

DMD controller 80 also contains various voltage regulation and conversion function 206 to power DMD 48 and to select DMD 48 attributes by maintaining various DMD pins at certain voltages as shown at 212.

The benefits of the present invention over the prior art are several and significant. The most evident advantage achieved is the ability to control and target the spatial distribution of illumination in a conventional microscope. Areas of the specimen to be illuminated can be very small—on the order of few microns—or the areas can be very large—on the order of hundreds of microns. Another major advantage of the present invention is the ability to customize the pattern of illumination which will be transmitted to the specimen in the microscope. This feature is of great benefit to researchers in the life sciences industry who need to illuminate or mask biological structures which are seldom geometric and uniform. By virtue of the ability to illuminate a specimen selectively, a researcher will be able to gain the ability to monitor and measure by photonic means select areas of the specimen with the same level of control.

Utilizing the digital mirror device which exhibits high speed, high pixel density, and a wide spectral bandwidth extending down into the near ultraviolet which is desirable in microscopy, provides an equally evident advantage in the ability to control the timing of illumination in a conventional microscope. Areas of the specimen can be illuminated in an infinite combination of repetitions and durations, ranging from pulses of a few hundreds of microseconds duration to continuous illumination. Conventional mechanical shutters can be installed into the illumination path of the microscope, but they are slower than the system of the present invention. Beam shape, for example, is not controllable with mechanical shutters alone because the aperture opening is typically predetermined. The present invention communicates directly with the DMD in a true black and white temporally-static manner unlike DMD projectors with standard pulse width modulated DMD interfaces. This eliminates any raster-type scanning of the mask pixels which reduce optical throughput and might adversely effect sensitive scientific experiments. The ability to customize the illumination of a microscope in real time using a translucent live-video interface is unique to the subject invention.

Thus, the present invention provides an illumination system for a conventional microscope which gives the user both spatial and temporal control over specimen illumination. The array of programmable micromirrors is inserted in the illumination axis such that when activated they allow light to be reflected along the illumination axis to the specimen plane. Each micromirror directs light toward a spatial position of the specimen plane which corresponds to the spatial position of the micromirror in a conjugate plane. The innovative software developed and described above enables the user to select areas in the field of view to be illuminated, or conversely to be masked and not illuminated by a light source. The user is also able to control the timing of illumination, ranging from single pulses of varying length, to continuous illumination.

As an example, a halogen light source 41, FIG. 2 may be used to transluminate from below a culture of living cells on the stage of a conventional microscope. Video camera 56 is mounted to the camera port of microscope 38 with the data output connected to the camera interface 152 of computer 106, FIG. 7 which displays the live-video image of the specimen on computer monitor 154. The researcher desires to illuminate, i.e., target, some of the cells in the field of view with a second light source and not other cells. Using computer mouse 158 and software 103 of this invention, the user draws translucent overlays on computer monitor 154 superimposed on but not obscuring the target cells. The user then selects to have these targets illuminated by a light source 46 such as an arc lamp used for epifluorescence excitation which is made to illuminate DMD 48 by way of optical element 58. Patterned light will be directed into microscope 38 along illumination axis 60 and will shine down from above onto the specimen culture at specimen plane 39. The spatial position of the mask-overlays relative to the specimen image correspond to the spatial position of the micromirrors of the DMD. The user then selects a time sequence and triggers the software. A spatial map of the overlays is encoded and directed to the DMD which reflects the light from light source 46 to the cell culture for a selected period of time. Thus, the researcher now has the ability to uniquely perform a photonic experiment on one part of a culture sample while simultaneously performing the control experiment or additional experiments on related parts of the same sample.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A spatial light modulator apparatus for an optical microscope system, the apparatus comprising:
    an optical head including:
        a mounting flange for mounting the optical head to a port of the microscope,
        a DMD for generating a pattern image of light,
        a light source mount for receiving a source of illumination, and
        one or more optical elements for directing light from the source of illumination to the DMD and to direct the pattern image generated by the DMD to the microscope;
    a DMD controller having a digital input and connected to the DMD for driving the individual micromirrors of the DMD to generate the pattern image;
    a pattern generation subsystem configured to output pattern image data; and
    a digital interface connected between the digital input of the DMD controller and the pattern generation subsystem, the digital interface configured to provide a digital drive signal to the DMD controller corresponding to the pattern image data.

2. The apparatus of claim 1 in which the DMD controller is mounted on the optical head adjacent the DMD.

3. The apparatus of claim 1 in which the digital interface is housed on a PC card received in a computer and wherein the pattern generation subsystem is operable on the computer.

4. The apparatus of claim 1 in which the optical head includes a housing with an illumination axis, the DMD is located on the housing on the illumination axis thereof and the mounting flange is located on the housing on the illumination axis thereof opposite the DMD.

5. The apparatus of claim 4 in which the light source mount is located on the optical head housing on an axis transverse to the illumination axis.

6. The apparatus of claim 1 in which the optical head further includes a light baffle positioned such that when the micromirrors of the DMD are in the off state, light reflected by the DMD is directed to the light baffle.

7. The apparatus of claim 1 in which the optical microscope has a field plane and the DMD and the optical elements of the optical head are configured to direct the pattern image generated by the DMD to the field plane of the optical microscope.

8. The apparatus of claim 1 in which the optical microscope has a field plane and the DMD and the optical elements of the optical head are configured to direct the pattern image generated by the DMD to a conjugate of the field plane of the optical microscope.

9. The apparatus of claim 1 further including a camera attached to the microscope, the camera having a field of view and wherein the optical elements are configured such that the DMD pattern image fills part or all of the field of view of the camera.

10. The apparatus of claim 1 further including a light source disposed in the light source mount.

11. The apparatus of claim 10 in which the light source is a halogen lamp, a flash lamp, an arc lamp, or a laser light source.

12. The apparatus of claim 1 in which the light source mount further includes a shutter assembly.

13. The apparatus of claim 1 in which the light source mount further includes a filter holder assembly.

14. The apparatus of claim 1 in which the optical head further includes a secondary light source mount.

15. The apparatus of claim 14 in which the secondary light source mount further includes a shutter assembly.

16. The apparatus of claim 14 in which the secondary light source mount further includes a filter holder assembly.

17. The apparatus of claim 1 in which the optical head further includes a beam splitter mount.

18. The apparatus of claim 1 in which the digital interface includes:
    a clock which provides a clock signal; and
    a logic device responsive to the pattern image data and the clock signal and configured to assign pixels to the pattern image data and to serialize the assigned pixels according to the clock signal to reformat the pattern image data to correspond to the spatial addressing of the DMD.

19. The apparatus of claim 18 in which the logic device is a programmable logic device or a field programmable gate array.

20. The apparatus of claim 18 further including a digital cable connecting the digital interface to the digital input of the DMD controller.

21. The apparatus of claim 18 in which the DMD controller is configured to buffer the reformatted mask image data and to load the memory cells of the DMD.

22. The apparatus of claim 18 in which the logic device is further configured to generate a plurality of timing signals based on the clock signal to synchronize serialization of the assigned pixels.

23. The apparatus of claim 22 in which the plurality of timing signals correspond to DMD address counter signals.

24. The apparatus of claim 23 in which several DMD address counter signals are multiplied in frequency by the logic device to provide faster global dark resets of the mirrors of the DMD.

25. The apparatus of claim 24 in which the logic device is further configured to provide a reset command, a new state command, and a hold command to reset, tilt to new state, or hold all of the mirrors of the DMD simultaneously.

26. The apparatus of claim 1 in which the optical microscope includes a camera for imaging the specimen viewed by the microscope live on a display.

27. The apparatus of claim 26 in which the pattern generation subsystem configured to output pattern image data comprises:
    a drawing editor responsive to an input device for drawing a pattern shape; and an alpha blending routine responsive to the camera and the drawing editor for representing the drawn pattern shape translucently on the display over the specimen image.

28. The apparatus of claim 27 in which the digital interface is responsive to the drawing editor to provide a digital drive signal which controls the DMD to generate the pattern image.

29. The apparatus of claim 27 in which said pattern generation subsystem further includes a set of stored calibration values and a spatial scale and offset routine interposed between the drawing editor and the digital interface and responsive to the stored calibration values for correlating the pixels of the drawn pattern shape to the pixels of the DMD.

30. An optical head for a spatial light modulator system, the optical head comprising:
   a mounting flange for mounting the optical head to a port of a microscope;
   a spatial light modulator device for generating a pattern image of light;
   a light source mount for receiving a source of illumination;
   one or more optical elements for directing light from the source of illumination to the spatial light modulator device and to direct the pattern image generated by the spatial light modulator device to a microscope; and
   a controller connected to the spatial light modulator device for driving the spatial light modulator device to generate the pattern image, the controller having a digital input responsive to a digital drive signal.

31. The optical head of claim 30 in which the spatial light modulator device is a DMD.

32. The optical head of claim 30 in which the optical head includes a housing with an illumination axis, the DMD is located on the housing on the illumination axis thereof and the mounting flange is located on the housing on the illumination axis opposite the DMD.

33. The optical head of claim 32 in which the light source mount is located on the optical head housing on an axis transverse to the illumination axis.

34. The optical head of claim 31 in which the optical head further includes a light baffle positioned such that when the micromirrors of the DMD are in the off state, light reflected by the DMD is directed to the light baffle.

35. The optical head of claim 30 in which the optical microscope has a field plane and the spatial light modulator device and the optical elements are configured to direct the pattern image generated by the spatial light modulator device to the field plane.

36. The optical head of claim 30 in which the optical microscope has a field plane and the spatial light modulator device and the optical elements are configured to direct the pattern image generated by the spatial light modulator device to a conjugate of the field plane.

37. The optical head of claim 30 further including a camera attached to the microscope having a field of view and wherein the optical elements of the optical head are configured such that the pattern image generated by the spatial light modulator device fills the field of view of the camera.

38. The optical head of claim 30 further including a light source disposed in the light source mount.

39. The optical head of claim 38 in which the light source is a halogen lamp, an arc lamp, a flash lamp, or a laser light source.

40. The optical head of claim 30 in which the light source mount further includes a shutter assembly.

41. The optical head of claim 30 in which the light source mount further includes a filter holder assembly.

42. The optical head of claim 30 further including a secondary light source mount.

43. The optical head of claim 42 in which the secondary light source mount includes a shutter assembly.

44. The optical head of claim 42 in which the secondary light source mount includes a filter holder assembly.

45. The optical head of claim 30 further including a beam splitter mount.

46. A spatial light modulator system for an optical microscope, the system comprising:
   an optical head including:
      a mounting flange for mounting the optical head to either the reflected light port or the transmitted light port of the microscope,
      a spatial light modulator for generating a pattern image of light,
      a light source mount for receiving a source of illumination, and
      one or more optical elements for directing light from the source of illumination to the spatial light modulator and to direct the pattern image generated by the spatial light modulator to the microscope, and
      a controller mounted on the optical head adjacent the spatial light modulator and having a digital input; and
   a computer including:
      a pattern generation subsystem configured to output pattern image data, and
      a digital interface PC card configured to provide a digital drive signal to the controller corresponding to the pattern image data generated by the pattern generation subsystem.

* * * * *